United States Patent [19]

Parker

[11] Patent Number: 4,602,099
[45] Date of Patent: Jul. 22, 1986

[54] ANTIRHINOVIRUS AGENTS

[75] Inventor: Roger A. Parker, Cincinnati, Ohio

[73] Assignee: Merrell Dow Pharmaceuticals Inc., Cincinnati, Ohio

[21] Appl. No.: 418,857

[22] Filed: Sep. 16, 1982

Related U.S. Application Data

[60] Continuation-in-part of Ser. No. 955,689, Oct. 30, 1978, abandoned, and Ser. No. 202,968, Nov. 3, 1980, abandoned, which is a division of Ser. No. 955,689, , which is a continuation-in-part of Ser. No. 751,139, Dec. 20, 1976, abandoned, which is a continuation-in-part of Ser. No. 347,232, Apr. 2, 1973, Pat. No. 4,000,164, Ser. No. 587,117, Jun. 16, 1975, Pat. No. 4,032,647, and Ser. No. 619,305, Oct. 3, 1975, Pat. No. 4,011,334.

[51] Int. Cl.$^4$ ............................................ C07D 307/58
[52] U.S. Cl. ...................................................... 549/479
[58] Field of Search ......................................... 549/479

[56] References Cited

U.S. PATENT DOCUMENTS 3,318,875  5/1967  Nobles ............................ 542/439 X
3,399,199  8/1968  Grier ................................... 544/398

FOREIGN PATENT DOCUMENTS 1934809  1/1970  Fed. Rep. of Germany .

OTHER PUBLICATIONS

The Merck Index, 10th Edition (Merck & Co. Inc., Rahway, N.J.) pp. 3-4, 162, 288, 375-6, 786, 1030 and 1078 (1983).
The Condensed Chemical Dictionary, 10th Edition (Van Nostrand Reinhold Co., N.Y.), pp. 9, 12, 115, 119, 483, and 906 (1981).

Primary Examiner—Richard L. Raymond
Attorney, Agent, or Firm—Edlyn S. Simmons

[57] ABSTRACT

Compounds of the following general structure are useful as antirhinovirus agents:

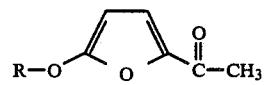

wherein R is a straight or branched hydrocarbon chain having from 12 to 16 carbon atoms and is saturated or is unsaturated having from 1 to 4 double bonds.

7 Claims, No Drawings

ANTIRHINOVIRUS AGENTS

This application is a continuation-in-part of copending U.S. application Ser. No. 955,689, filed Oct. 30, 1978, now abandoned, and of copending U.S. application Ser. No. 202,968, filed Nov. 3, 1980, now abandoned which is a division of the aforesaid U.S. application Ser. No. 955,689, which is a continuation-in-part of U.S. application Ser. No. 751,139, filed Dec. 20, 1976, abandoned, which is a continuation-in-part of U.S. applications Ser. Nos. 347,232, filed Apr. 2, 1973, now U.S. Pat. No. 4,000,164; 587,117, filed June 16, 1975, now U.S. Pat. No. 4,032,647; and 619,305, filed Oct. 3, 1975, now U.S. Pat. No. 4,011,334.

FIELD OF INVENTION

This invention relates to 5-substituted furan methyl ketones and their use as antirhinovirus agents.

SUMMARY OF INVENTION

Compounds of the following general Formula I are useful as antirhinovirus agents:

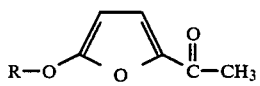

Formula I

In the above general Formula I, R is a straight or branched saturated hydrocarbon chain having from 12 to 16 carbon atoms or a straight or branched unsaturated hydrocarbon chain having from 12 to 16 carbon atoms and from 1 to 4 double bonds.

DETAILED DESCRIPTION OF THE INVENTION

In the above general Formula I, the substituent R is a straight or branched saturated hydrocarbon chain having from 12 to 16 carbon atoms, in which case the R—O— group represents an alkoxy chain which is straight or branched, or R is a straight or branched unsaturated hydrocarbon chain having from 12 to 16 carbon atoms and from 1 to 4 double bonds in which case the R— group may be represented as

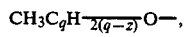

wherein q is an integer of from 11–15 and z is an integer of from 1–4 which corresponds to the number of double bonds in R, and the hydrocarbon chain is straight or branched.

Illustrative examples of straight or branched saturated hydrocarbon chains which R may represent are, for example, dodecyl, tridecyl, tetradecyl, 2,4-diethylnonyl, 1-methylundecyl, pentadecyl, hexadecyl, 5-propylundecyl and 3,7,11-trimethyldodecyl.

Illustrative examples of straight or branched unsaturated hydrocarbon chains containing from 1 to 4 double bonds which R may represent are, for example, 10-dodecenyl, 12-methyl-3-tridecenyl, 11-tetradecenyl, 3,6-hexadecadienyl, 5-ethyl-2,4,6,8-dodecatetraenyl, 3,7,11-trimethyl-2,6,11-dodecatrienyl, 1-vinyl-1,5,9-trimethyl-4,8-decadienyl and 1,6,8-tridecatrien-4-yl.

The compounds of Formula I wherein R is a straight or branched hydrocarbon chain of 13 to 15 carbon atoms represent a preferred embodiment of this invention. Those compounds of Formula I wherein R has 14 carbon atoms are more preferred.

Another preferred embodiment of this invention is the use of compounds of general Formula I as antirhinovirus agents. The use of compounds of general Formula I wherein R has 13 to 15 carbon atoms are preferred, with compounds of Formula I wherein R is tetradecyl and those wherein the R group is a branched 15 carbon chain being more preferred.

The compounds of general Formula I are described as intermediates for the preparation of hypolipidemic agents in parent U.S. application Ser. No. 347,232, filed Apr. 2, 1973, now U.S. Pat. No. 4,000,164.

Illustrative examples of compounds of general Formula I are the following:
methyl 5-tetradecyloxy-2-furyl ketone
methyl 5-(cis-9-pentadecenyloxy)-2-furyl ketone
methyl 5-(9,12,15-hexadecatrienyloxy)-2-furyl ketone
methyl cis-5-(11-tetradecenyloxy)-2-furyl ketone
methyl 5-(2-methyltetradecyloxy)-2-furyl ketone
methyl 5-(3,7,11-trimethyldodecyloxy)-2-furyl ketone
methyl 5-pentadecyloxy-2-furyl ketone
methyl 5-dodecyloxy-2-furyl ketone
methyl 5-tridecyloxy-2-furyl ketone
methyl 5-hexadecyloxy-2-furyl ketone
methyl 5-(1-methyldodecyloxy)-2-furyl ketone
methyl 5-(3,7-dimethyl-8-dodecenyloxy)-2-furyl ketone
methyl 5-(9,12-tridecadienyloxy)-2-furyl ketone
methyl 5-(3,7-dimethyl-2,6,9-decatrienyloxy)-2-furyl ketone The compounds of general Formula I are useful as antirhinovirus agents. The rhinovirus subgroup is a member of the picornavirus group and contains over 100 different antigenic types and is known to be responsible for many of the symptoms attendant respiratory infections. The name rhinovirus is indicative of the prominent nasal involvement seen in infections with these viruses, resulting in syndromes characteristic of the common cold. Rhinoviruses have been classified as serotypes 1 to 89 and subtypes 1A(88,89,90) with at least 20 more types to be added to the classification. Experimental studies indicate that nasal mucosal cells are more susceptible to rhinovirus than are the cells of the lower respiratory tract. The symptoms of rhinovirus infection have also been produced experimentally be dropping small amounts of the virus on the conjunctiva, indicating that the eye is another susceptible site of infection. Developed rhinovirus infection is characterized by hyperemia and edema of the musous membrane with exudation of serous and mucinous fluid. The nasal cavities are narrowed by thickening of the membrane and engorgement of the turbinates.

The compounds described herein have been found to be effective antiviral agents against numerous types of rhinovirus, rendering said compounds useful in treating the symptoms of a rhinovirus infection in hosts susceptible to said infections, including humans and certain anthropoid apes, such as the chimpanzee. It is known in the art that several test systems can be employed to measure antiviral activity against rhinovirus. For example, antirhinovirus activity can be measured using a placque assay or tube test wherein the activity of the compound against virus challenge in a cell system is measured. Using a variety of test systems, it was found that compounds of general Formula I are effective antirhinovirus agents when the test compound is given prior to, concurrently with, or subsequent to virus challenge. The utility of the compounds described herein as antirhinovirus agents has been demonstrated in a variety of test systems. For example, using HeLa cell cultures to which a rhinovirus challenge of from 30 to 100 $TCID_{50}$ is added concurrently with test compounds at a concentration of 4, 20, or 100 μg/ml, after which the cell cultures are incubated for 48 hours, it was found upon microscopic examination of the cell cultures that compounds of general Formula I markedly inhibit the cytopathic effect of the virus when compared to cell cultures containing virus challenge alone. For example, when the compound of Example 1 at a concentration of 4 μg/ml was added to cell cultures together with a rhinovirus challenge of 100 $TCID_{50}$, the cytopathic effect of virus was inhibited by 87% when compared to control. In a virus yield reduction test using HeLa cells, it was found that the tissue culture $ED_{50}$ of the compound of Example 1 is 0.3 μg/ml. The compounds of general Formula I are also useful therapeutically in treating rhinovirus infections in that said compounds are effective in diminishing or blocking virus maturation. The compounds of the invention inactivate rhinovirus extracellularly or intracellularly.

It is known that rhinovirus is readily transmitted from one susceptible host to another as commonly occurs, for example, among family members, in classrooms, and in military populations. Rhinovirus is shed from the nose, mouth and eyes of infected individuals, is carried on the skin, particularly on the hands and face, and may be released into the environment by handling objects and by coughing, sneezing, breathing and speaking. Susceptible individuals may become exposed to rhinovirus infection by direct physical contact with infected individuals, by handling rhinovirus-contaminated objects, or by breathing rhinovirus-bearing air. Interpersonal transmission of rhinovirus infection may be diminished by application of a compound of general Formula I to the skin of infected individuals, preventing the transfer of viable rhinovirus to other individuals or to objects; to the skin of uninfected individuals, preventing viable rhinovirus from being carried thereon to the mucosa or the conjunctiva of such uninfected individuals; to environmental objects, preventing the transfer of viable rhinovirus to uninfected individuals contacting them; or to the air of enclosed spaces, preventing the inhalation by uninfected individuals of viable rhinovirus shed by infected individuals. For such purposes the compound may be, for example, in the form of a skin cream, gel, lotion or powder, a detergent composition or disinfectant rinse, or an aerosol or spray.

In the treatment of symptoms of rhinovirus infection, the compounds of general Formula I can be administered orally, topically, for example, intranasally, and parenterally, for example, intramuscularly. Topical administration is preferred. The compounds may be applied topically to the skin or the membranes of the nose, mouth and eye, replication of rhinovirus being blocked at the site of administration and, by means of transdermal or transmucosal absorption, systemically.

The compounds are administered preferably in the form of a pharmaceutical preparation to a host either prior to or after invasion of virus. For prophylactic treatment, it is contemplated that an antirhinovirus effective amount of compound be administered for about 1 to 5 days prior to anticipated exposure to virus and for about 5 to 10 days subsequent to exposure or for about 5 to 15 days subsequent to exposure to rhinovirus. For therapeutic treatment, for example, an antirhinovirus effective amount of compound may be administered after exposure to rhinovirus for a period of about two weeks.

For prophylactic or therapeutic treatment of rhinovirus infection, any antirhinovirus effective amount of a compound of general Formula I may be employed. The amount of compound required to achieve an antirhinovirus effect will vary depending primarily upon the mode of administration. For therapeutic treatment, the amount of compound administered will also vary depending on the severity of the infection. For oral or parenteral treatment the amount of compound administered will vary from about 0.1 mg/kg to 1500 mg/kg of body weight of the patient. Preferably, the amount of compound administered will vary from about 1 mg/kg to about 250 mg/kg. Typically a unit dose containing about 500 mg of compound administered from 1 to 6 times daily will achieve the desired effect. For topical treatment, an amount sufficient to coat the area to be treated of a composition containing an antirhinovirus effective concentration of compound will be applied to the mucosa, conjunctiva or epidermis. Such compositions will typically contain from about 0.001 to about 50%, preferably from 0.01 to 5% of a compound of general Formula I in a liquid or solid carrier. An antirhinoviral effect will, for example, be attained by 0.1 ml of a nose drop contaning 3 μg/ml of compound instilled into each nostril from 1 to 8 times daily. Preferably, such a nosedrop will be administered by means of a metered spray device, ensuring that a uniform, widely distributed dosage is applied to the nasal mucosa.

The active compound may also be administered by means of a sustained release system whereby the compound of general Formula I is gradually released at a controlled, uniform rate from an inert or bioerodible carrier, by means of diffusion, osmosis, or disintegration of the carrier, during the treatment period. Controlled release drug delivery systems may be in the form of a patch or bandage applied to the skin or to the buccal, sublingual or intranasal membranes, an ocular insert placed in the cul de sac of the eye, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of Formula I. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysuphones, polysiloxanes and polyimides, and mixtures, lamina, and copolymers thereof. The compound of Formula I may be incorporated in the sustained release carrier in a pure form or may be dissolved in any suitable liquid or solid vehicle, including the polymer of which the sustained release carrier is formed.

The compounds of general Formula I together with suitable pharmaceutical carriers can be in the form of solid unit dosage forms such as tablets, capsules, powders and troches, in the form of a suppository, or embedded in a a polymeric matrix. The powders can be administered orally, topically or by insufflation. In preparation of solid unit dosage forms it may be desirable to micronize the compound to be employed. In solid unit dosage forms the compounds can be combined with conventional carriers, for example, binders, such as acacia, corn starch or gelatin, disintegrating agents, such as corn starch, guar gum, potato starch or alginic acid, lubricants, such as stearic acid or magnesium stearate, and inert fillers, such as lactose, sucrose or corn starch.

The compounds of general Formula I may also be administered as liquid suspensions or solutions using a sterile liquid, such as an oil, water, an alcohol, or mixtures thereof, with or without the addition of a pharmaceutically suitable surfactant, suspending agent, or emulsifying agent for oral, topical or parenteral administration. A particularly suitable mode of administration is a liquid formulation of the compounds applied directly to the nasal cavity, for example, in the form of a nose drop or spray. Liquid formulations may also be administered directly to the eye as an eye drop, administered orally, or applied to the membranes of the oral cavity and pharynx as a gargle or mouthwash. Liquid formulations, including gels and ointments, may take the form of skin lotions and creams for application to the hands and face. Such lotions and creams may contain emollients, perfumes, or pigments to form cosmetically acceptable moisturizers, astringents, shaving lotions, colognes, cosmetic foundations, and similar preparations. A skin lotion for use on the hands comprising a compound of general Formula I is especially preferred for prevention of transfer of rhinovirus infection from infected to uninfected individuals. In general, a topical antiviral composition of this invention will contain from about 0.01 g to about 5 g of a compound of general Formula I per 100 ml of the composition.

For liquid preparations, the compounds of Formula I can be formulated suitably with oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides; with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 400; with petroleum hydrocarbons, such as mineral oil and petrolatum; with water; or mixtures thereof; with or without the addition of a pharmaceutically suitable surfactant, suspending agent or emulsifying agent.

Peanut oil and sesame oil are particularly useful in preparation of formulation for intramuscular injection. Oils can also be employed in the preparation of formulations of the soft gelatin type and suppositories. Water, saline, aqueous dextrose and related sugar solutions, and glycerols, such as polyethyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and polyoxyethylenepolyoxypropylene coploymers; and amphoteric detergents, for example, alkyl $\beta$-aminopropionates and 2-alkylimidazoline quaternary ammonium salts; and mixtures thereof. Detergent compositions may be in bar, powder or liquid form and may incorporate foam builders, viscosity control agents, antimicrobial agents, preservatives, emollients, coloring agents, perfumes, and solvents. Such soap and detergent formulations may be applied to textiles, to environmental surfaces and, preferably, to the skin. A preferred detergent composition is a liquid soap or synthetic detergent composition comprising from about 0.01 to about 5 g of a compound of Formula I per 100 ml of the composition.

Aerosol or spray preparations containing compounds of general Formula I may be used as space disinfectants or for application to environmental surfaces, to skin, or to mucous membranes. Such compositions may contain a micronized solid compound of Formula I or a solution of a compound of Formula I and may also contain solvents, buffers, surfactants, perfumes, antimicrobial agents, antioxidants and propellants. Such compositions may be applied by means of a propellant under pressure or may be applied by means of a compressible plastic spray bottle, a nebulizer or an atomizer without the use of a gaseous propellant. A preferred aerosol or spray composition is a nasal spray.

Pharmaceutical compositions for treatment of rhinovirus infection may contain, in addition to an antirhinoviral amount of a compound of general Formula I in an appropriate pharmaceutical carrier, one or more agents useful for the treatment of symptoms of rhinovirus infection. Agents known in the art to be useful for symptomatic treatment of rhinovirus infection include antihistamines, decongestants, antipyretics, analgesics, antitussives, expectorants, local anesthetics and vitamin C. Examples of suitable antihistamines include terfenadine, doxylamine, chlorpheniramine, brompheniramine, methapyrilene, phenindamine, phenyltoloxamine, azatadine, triprolidine and dimethindine and their pharmaceutically acceptable acid addition salts. Examples of suitable decongestants include ephedrine, levodesoxyephedrine, phenylephrine, xylometazoline, naphazoline, tetrahydrozoline, phenylpropanolamine, cyclopentamine, propylhexedrine, tuaminoheptane and methoxyphenamine and their pharmaceutically acceptable acid addition salts. Examples of suitable antitussives include codeine, hydrocodone, ethylmorphine, noscapine, dextromethorphan, carbetapentane and diphenhydramine and their pharmaceutically acceptable salts. Examples of suitable expectorants include guaifenesin, terpin hydrate, sodium glycerophosphate, potassium guaiacolsulfonate, ammonium chloride, ipecac, eucalyptus, chloroform and menthol. Examples of suitable analgesic and antipyretic agents include aspirin, salicylic acid, salicylamide, acetanilide, acetophenetidin, acetaminophen, antipyrine and aminopyrine. Examples of suitable local anesthetics include benzocaine, benzyl alcohol, and phenol and its pharmaceutically acceptable salts. The amount of each medicament included in the antirhinoviral pharmaceutical composition effective for the symptomatic treatment of rhinovirus infection will vary according to the composition of the carrier and the agent included in it.

Illustrative examples of suitable pharmaceutical and detergent formulations are set forth hereinbelow.

The ketone compounds of general Formula I may be prepared by treating one equivalent of the corresponding carboxylic acid derivatives with two equivalents of methyllithium as generally described by Fieser and Fieser, *Reagents for Organic Synthesis*, J. Wiley and Sons, Inc., New York, p. 688 (1967). This reaction is suitably carried out in solvents such as ether, tetrahydrofuran, p-dioxane, dimethoxyethane or diethyleneglycol dimethylether at temperatures of from −10° C. to the reflux temperature of the solvent for from ½ hour to 10 hours.

The ketone compounds of general Formula I may also be prepared by the reaction of methyl magnesium bromide and the imidazolide derivative of an appropriately R—O substituted furancarboxylic acid derivative wherein R has the meaning defined in general Formula I. This reaction is carried out in a solvent such as ether, tetrahydrofuran, dioxane, dimethoxyethane, or acetonitrile. The reaction mixture is initially cooled to −10° C., after which the temperature is elevated to from about 25° C. to the reflux temperature of the solvent, and the reaction time varies from about ½ hour to 10 hours. The imidazolide derivative is obtained by treating an appropriately R—O substituted furancarboxylic acid derivative with N,N'-carbonyldiimidazole or by treatment of the R—O substituted furancarboxylic acid chloride, obtained by treating the substituted carboxylic acid with thionyl chloride, with two equivalents of imidazole, as generally described by H. A. Staab, *Angew. Chem. Internat. Edit.* 1 351 (1962).

The compounds of general Formula I may also be prepared by a Friedel-Crafts acylation of an appropriately R—O substituted furan, wherein R has the meaning defined in general Formula I, with an acetyl halide of the formula

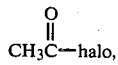

wherein halo is halogen, preferably chlorine or bromine. This reaction is carried out in the presence of an acid catalyst, for example, borontrifluoride-etherate, stannic chloride, zinc chloride, hydriodic acid or orthophosphoric acid, and optionally in the presence of a solvent, for example, methylene chloride, nitromethane or benzene. Suitable temperatures for this reaction vary from −20° C. to the reflux temperature of the solvent and the reaction time varies from about ½ hour to 10 hours.

The R—O— substituted furan derivative employed herein can also be obtained by thermodecarboxylation at a temperature above 150° C. of an appropriately R—O— substituted furonic acid by procedures known in the art.

The R—O— substituted furancarboxylic acid derivative used herein can be prepared by aromatic nucleophilic substitution as generally described in J. March, *Advanced Organic Chemistry: Reactions, Mechanisms and Structure*, McGraw-Hill, p. 500 (1968), as outline below.

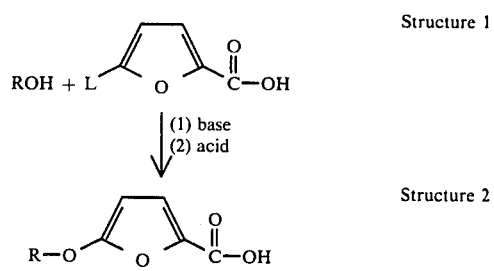

In the above general reaction, R has the meaning defined in general Formula I and L represents a leaving group, such as nitro, fluoro, chloro, bromo, or iodo, the preferred leaving group being chloro.

The above reaction may be carried out with or without a solvent. Suitable solvents for the reaction include benzene, xylene, toluene, chlorinated hydrocarbon solvents, such as chlorobenzene, ethers, such as bis(2-methoxyethyl)ether, 1,2-dimethoxyethane or anisole, hexamethylphosphoric triamide (HMPA), dimethylformamide, dimethylacetamide, 1-methyl-2-pyrrolidone or pyridine. Preferred solvents are xylene, toluene and dimethylacetamide. Copper metal or a salt such as cuprous chloride may optionally be added to the reaction. Suitable bases for the reaction include sodium or potassium metal, sodium hydride, potassium amide, potassium tert-butoxide or other strong bases, such as potassium carbonate, potassium hydroxide, sodium hydroxide and sodium carbonate. The temperature of the reaction varies from about 25° C. to the reflux temperature of the solvent and the reaction time varies from about 1 hour to about 7 days. Following completion of the reaction, the carboxylate salt derivative is treated with a mineral or organic acid to give compounds of structure 2.

Alcohols, as represented by ROH, which find use in the above general reaction, are commercially available or may be prepared by reduction of the corresponding carboxylic acid or aldehyde.

The furoic acid derivatives represented by compounds of structure 1 may be prepared by several methods, as described in *The Furans*, by A. P. Dunlop and F. N. Peters, Reinhold Publishing Corp., pp. 80–169 (1953).

The following specific examples further illustrate the invention.

EXAMPLE 1

Methyl 5-tetradecyloxy-2-furyl ketone (A) A mixture of 125.0 g (0.652 mole) of 5-bromo-2-furoic acid, 210.0 g (0.978 mole) of 1-tetradecanol, 183.0 g (1.630 mole) of potassium tert-butoxide and 2500 ml of dimethylacetamide is heated with stirring. The tert-butanol formed in the reaction is allowed to distill off, then the mixture is heated to reflux with stirring for 48 hours. To the cooled mixture is added 6 liters of ice water, and the mixture is acidified with malonic acid. The resulting precipitate is collected, dried and recrystallized twice from methanol to give 82.0 g (29%) of 5-tetradecyloxy-2-furoic acid, M.P. 112°–115° C. (dec.).

(B) A mixture of 82.0 g (0.235 mole) of 5-tetradecyloxy-2-furoic acid, 41.0 g (0.235 mole) of N,N'-carbonyldiimidazole and 800 ml tetrahydrofuran is stirred at room temperature during which time carbon dioxide gas is evolved. The reaction mixture is cooled to 0° C. to give N-[5-tetradecyloxy-2-furoyl]imidazole. The N-substituted imidazole, 50.0 g (0.134 mole) in 500 ml tetrahydrofuran is cooled in an ice bath. An equivalent amount of methyl magnesium bromide (50 ml of a 3M solution in ether) is slowly added over a 2-hour period to the stirred mixture. The reaction is stirred for an additional 3 hours, then excess (500 ml) of 2N HCl is added and the product extracted into ether. The ether extract is separated, washed with water, dried over sodium sulfate, filtered, and evaporated to dryness to give methyl 5-tetradecyloxy-2-furyl ketone, M.P. 70°–72° C.

EXAMPLE 2

Methyl 5-(cis-9-pentadecenyloxy)-2-furyl ketone

A mixture of 57.2 (0.300 mole) of 5-bromo-2-furoic acid, 121.0 g (0.45 mole) of cis-9-pentadecenol, 18.0 g (0.750 mole) of sodium hydride and 2 liters of p-xylene are heated to reflux for 48 hours. The mixture is allowed to cool, then is acidified with acetic acid and diluted with 2 liters of water. The organic layer is separated, dried, evaporated to dryness, and the residue recrystallized from hexane to give 5-(cis-9-pentadecenyloxy)-2-furoic acid.

When in the procedure of Example 1(B) an appropriate amount of 5-(cis-9-pentadecenyloxy)-2-furoic acid is substituted for 5-(tetradecyloxy)furoic acid, methyl 5-(cis-9-pentadecenyloxy)-2-furyl ketone is obtained.

EXAMPLE 3

Methyl 5-(9,12,15-hexadecatrienyloxy)-2-furyl ketone

A mixture of 57.0 g (0.300 mole) of 5-bromo-2-furoic acid, 119.0 g (0.450 mole) of 9,12,15-hexadecatrienol, and 84 g (0.750 mole) of potassium tert-butoxide in dry toluene is stirred with heating. The tert-butanol formed in the reaction is allowed to distill off, and the mixture is refluxed at 110° C. with stirring for 48 hours. The mixture is allowed to cool, then is acidified with acetic acid and diluted with ice water. The toluene organic layer is separated, washed with water, then extracted three times with 5% sodium bicarbonate solution. The combined aqueous extracts are cooled and acidified with 10% HCl solution to give 5-(9,12,15-hexadecatrienyloxy)-2-furoic acid.

When in the procedure of Example 1(B) an appropriate amount of 5-(9,12,15-hexadecatrienyloxy)-2-furoic acid is substituted for 5-tetradecyloxy-2-furoic acid, methyl 5-(9,12,15-decatrienyloxy)-2-furyl ketone is obtained.

EXAMPLE 4

Methyl cis-5-(11-tetradecenyloxy)-2-furyl ketone (A) 8.8 g (0.0414 mole) of cis-11-tetradecen-1-ol was combined with 4.0 g (0.0829 mole) of sodium hydroxide (50% in oil) in 200 ml of dry toluene and heated to reflux with stirring for 3 hours. 6.1 g (0.414 mole) of 5-chloro-2-furoic acid was added, followed by 25 ml of hexamethylphosphoric triamide (HMPA), and the reaction mixture refluxed with stirring for 20 hours, cooled, and acidified with acetic acid. The mixture was extracted into ether and the organic layer washed with water and with brine and evaporated to yield cis-5-(11-tetradecenyloxy)furan-2-carboxylic acid, M.P. 89°–90° C.

(B) A mixture of 4.2 g (0.013 mole) of cis-5-(11-tetradecenyloxy)furan-2-carboxylic acid and 50 ml of anhydrous ether was stirred at room temperature and 20.2 ml (0.0313 mole) of methyllithium (1.55 molar in hexane) added over 15 minutes. The mixture was stirred at room temperature for 3 hours and poured into saturated ammonium chloride solution. About 10 ml of glacial acetic acid was added and the phases separated. The ether layer was washed with water and evaporated to dryness to give a light yellow semisolid residue which was recrystallized twice from methanol to give methyl cis-5-(11-tetradecenyloxy)-2-furyl ketone, M.P. 3638° C.

EXAMPLE 5

Methyl 5-(2-methyltetradecyloxy)-2-furyl ketone (A) In the procedure of Example 4(A), 2-methyltetradecanol was substituted for cis-11-tetradecenol and 5-bromo-2-furoic acid substituted for 5-chloro-2-furoic acid to yield 5-(2-methyltetradecyloxy)-2-furancarboxylic acid, M.P. 88°–90° C.

(B) In the procedure of Example 4(B) 5-(2-methyltetradecyloxy)-2-furancarboxylic acid was substituted for cis-5-(11-tetradecenyloxy)-2-furancarboxylic acid to yield methyl 5-(2-methyltetradecyloxy)-2-furyl ketone, M.P. 45°–47° C.

EXAMPLE 6

Methyl 5-(3,7,11-trimethyldodecyloxy)-2-furyl ketone (A) In the procedure of Example 4(A), 3,7,11-trimethyldodecanol was substituted for cis-11-tetradecenol and 5-bromo-2-furoic acid substituted for 5-chloro-2-furoic acid to yield 5-(3,7,11-trimethyldodecyloxy)-2-furancarboxylic acid, M.P. 70°–73° C.

(B) In the procedure of Example 4(B), 5-(3,7,11-trimethyldodecyloxy)-2-furancarboxylic acid was substituted for cis-5-(11-tetradecenyloxy)furancarboxylic acid, to yield as a pale yellow oil, methyl 5-(3,7,11-trimethyldodecyloxy)-2-furyl ketone, B.P. 165° C. (0.25 mm Hg.).

EXAMPLE 7

Methyl 5-pentadecyloxy-2-furyl ketone

In the procedure of Example 4, 1-pentadecanol was substituted for cis-11-tetradecen-1-ol to yield methyl 5-pentadecyloxy-2-furyl ketone, M.P. 67°–68° C.

EXAMPLE 8

Methyl 5-dodecycloxy-2-furyl ketone

In the procedure of Example 4, 1-dodecanol was substituted for cis-11-tetradecen-1-ol to yield methyl 5-dodecyloxy-2-furyl ketone, M.P. 66°–67° C.

EXAMPLE 9

Methyl 5-tridecyloxy-2-furyl ketone

In the procedure of Example 4, 1-tridecanol was substituted for cis-11-tetradecen-1-ol to yield methyl 5-tridecyloxy-2-furyl ketone, M.P. 61°–62° C.

EXAMPLE 10

Methyl 5-hexadecyloxy-2-furyl ketone

In the procedure of Example 4 1-hexadecanol was substituted for cis-11-tetradecen-1-ol to yield methyl 5-hexadecyloxy-2-furyl ketone, M.P. 72°–76° C.

EXAMPLE 11

| Solution | |
|---|---|
| Methyl 5-(3,7,11-trimethyldodecyloxy)-2-furyl ketone | 0.85 g |
| Alcohol | 78.9 ml |
| Isopropyl Myristate | 5.0 g |
| Polyethylene Glycol 400 | 10.0 g |
| Purified Water qs ad | 100.0 ml |

Combine the alcohol, isopropyl myristate and polyethylene glycol 400 and dissolve the drug substance therein. Add sufficient purified water to give 100 ml.

EXAMPLE 12

| Tablet | |
|---|---|
| | For 15,000 |
| Methyl 5-tridecyloxy-2-furyl ketone | 75 g |
| Lactose | 1.216 Kg |
| Corn Starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:
  Magnesium Stearate: 0.015 Kg
  Corn Starch qs ad: 1.725 Kg
Compress on a suitable tablet machine to a weight of 0.115 g/tablet.

EXAMPLE 13

| Soft Gelatin Capsule | |
|---|---|
| Methyl 5-tetradecyloxy-2-furyl ketone | 0.25 Kg |
| Polysorbate 80 | 0.25 Kg |
| Corn Oil qs ad | 25.0 Kg |
| Mix and fill into 50,000 soft gelatin capsule. | |

EXAMPLE 14

| IM Injections | |
|---|---|
| A. Oil Type: | |
| Methyl cis-5-(11-tetradecenloxy)-2-furyl ketone | 25.0 mg |
| BHA, BHT aa | 0.01% w/v |
| Peanut Oil or Sesame Oil qs | 1.0 ml |
| B. Suspension Type: | |
| Methyl cis-5-(11-tetradecenyloxy)-2-furyl ketone, micronized | 25.0 mg |
| Sodium Carboxymethylcellulose | 0.5% w/v |
| Sodium Bisulfide | 0.02% w/v |
| Water for Injection, qs | 1.0 ml |

EXAMPLE 15

| Powder | |
|---|---|
| | % w/w |
| Methyl 5-pentadecyloxy-2-furyl ketone | 1.0 |
| Silicon dioxide, anhydrous | 0.5 |
| Corn starch, lactose, fine powder aa | qs |

EXAMPLE 16

| Nasal Drop or Spray | |
|---|---|
| Methyl 5-tetradecyloxy-2-furyl ketone | 0.10 g |
| Ethyl oleate | 20.0 g |
| Butylated hydroxyanisole | 4.0 mg |
| Poloxamer 235 | 25.0 g |
| Benzyl alcohol | 4.7 ml |
| Sorensen Phosphate Buffer Solution[1] qs | 500.0 ml |

[1]A 50/50 mixture of sodium biphosphate solution and sodium phosphate solution rendered isotonic by addition of sodium chloride.

EXAMPLE 17

| Nasal Drop or Spray | |
|---|---|
| Methyl 5-(2-methyltetradecyloxy)-2-furyl ketone | 0.125 g |
| Isostearic acid | 5.0 g |
| Poloxamer 215 | 12.5 g |
| NaOH qs ad | pH 7.6 |
| Benzyl alcohol | 4.7 ml |
| Mannitol powder | 25.35 g |
| Deionized water qs | 500.0 ml |

EXAMPLE 18

| Hand Lotion | |
|---|---|
| Methyl 5-tetradecyloxy-2-furyl ketone | 0.15 g |
| Isostearic acid | 10.0 g |
| Stearic acid | 8.0 g |
| Poloxamer 235 | 5.0 g |
| Propylene glycol | 10.0 g |
| Deionized water qs | 100.0 ml |

EXAMPLE 19

| Liquid Soap | |
|---|---|
| Methyl 5-tetradecyloxy-2-furyl ketone | 0.3 g |
| Green soap tincture, NF | 100.0 ml |

EXAMPLE 20

| Liquid Detergent | |
|---|---|
| Methyl 5-tetradecyloxy-2-furyl ketone | 0.025 g |
| Miranol SM Concentrate (1-Carboxymethyl-3,4-dihydro-1-(2-hydroxyethyl)-2-nonyl-1H—imidazolium hydroxide, disodium salt) | 25.0 g |
| Laureth-4 | 2.0 g |
| Deionized water, qs | 100 ml |

EXAMPLE 21

| Solution | |
|---|---|
| Methyl 5-tetradecyloxy-2-furyl ketone | 0.05 g |
| 2-Pyrrolidone | 10.02 g |

EXAMPLE 22

| Nasal Drop or Spray | |
|---|---|
| Methyl 5-tetradecyloxy-2-furyl ketone | 0.4 g |

| -continued | |
| --- | --- |
| Nasal Drop or Spray | |
| Corn Oil | 40.0 g |
| Butylhydroxyanisole | 0.008 g |
| Poloxamer 403 | 50.0 g |
| Methylparaben | 1.8 g |
| Propylparaben | 0.2 g |
| Sodium phosphate, dried | 4.57 g |
| Sodium Phosphate, monobasic, monohydrate | 4.44 g |
| Sodium Chloride | 4.63 g |
| Purified water q.s. | 1 L |

I claim:

1. A compound of the formula

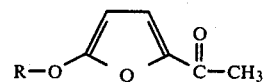

wherein R is a straight or branched saturated hydrocarbon chain having from 12 to 16 carbon atoms or a straight or branched unsaturated hydrocarbon chain having from 12 to 16 carbon atoms and from 1 to 4 double bonds.

2. A compound of claim 1 wherein R has from 13 to 15 carbon atoms.

3. A compound of claim 1 wherein R has 14 carbon atoms.

4. A compound of claim 1 wherein the R has 15 carbon atoms and is branched.

5. A compound of claim 1 which is methyl 5-tetradecyloxy-2-furyl ketone.

6. A compound of claim 1 which is methyl 5-(2-methyltetradecyloxy)-2-furyl ketone.

7. A compound of claim 1 which is 5-(3,7,11-trimethyldodecyloxy)-2-furyl ketone.

* * * * *